US006942862B2

(12) United States Patent
Cheever et al.

(10) Patent No.: US 6,942,862 B2
(45) Date of Patent: Sep. 13, 2005

(54) METHODS AND COMPOSITIONS TO GENERATE IMMUNITY IN HUMANS AGAINST SELF TUMOR ANTIGENS BY IMMUNIZATION WITH HOMOLOGOUS FOREIGN PROTEINS

(75) Inventors: Martin A. Cheever, Mercer Island, WA (US); Mary L. Disis, Renton, WA (US)

(73) Assignee: University of Washington, Seattle, WA (US)

( * ) Notice: Subject to any disclaimer, the term of this patent is extended or adjusted under 35 U.S.C. 154(b) by 90 days.

(21) Appl. No.: 09/088,951

(22) Filed: Jun. 2, 1998

(65) Prior Publication Data

US 2002/0019331 A1 Feb. 14, 2002

Related U.S. Application Data

(63) Continuation-in-part of application No. 08/625,101, filed on Apr. 1, 1996, now Pat. No. 5,869,445.
(60) Provisional application No. 60/048,406, filed on Jun. 3, 1997.

(51) Int. Cl.⁷ .......................... A61K 39/00; A61K 38/17
(52) U.S. Cl. .................................. 424/185.1; 424/277.1
(58) Field of Search .......................... 424/185.1, 277.1, 424/130.1; 514/2; 530/806

(56) References Cited

U.S. PATENT DOCUMENTS

| | | | |
|---|---|---|---|
| 4,205,130 A | 5/1980 | Vihko ........................ 435/196 |
| 4,267,272 A | 5/1981 | Josephson ...................... 435/7 |
| 4,510,239 A | 4/1985 | Miller et al. ................... 435/7 |
| 5,679,647 A | * 10/1997 | Carson et al. |
| 5,719,030 A | 2/1998 | Kuroiwa et al. ............. 435/7.1 |
| 5,738,867 A | 4/1998 | Spitler ........................ 424/450 |
| 5,925,362 A | 7/1999 | Spitler et al. ............ 424/277.1 |
| 5,976,546 A | 11/1999 | Laus et al. ................ 424/192.1 |
| 6,080,409 A | * 6/2000 | Laus et al. |

FOREIGN PATENT DOCUMENTS

| | | |
|---|---|---|
| CA | 1 185 525 | 4/1985 |
| WO | WO 95/04548 | 2/1995 |
| WO | WO 98/46769 | 10/1998 |

OTHER PUBLICATIONS

Chatta et al, Induction of immunity to rat prostatic phosphatase (PAP): Implications for prostate cancer immunotherapy. Proc. Annu Meet Am Assoc Cancer Res, Mar. 1997, vol. 38, p. A2703.*
Dryberg and Oldstone, Peptides as Probes ro Study Molecular Mimicry and Virus–Induced Autoimmunity, in: CCurrent Topics in Microbiology and Immunology, 1986, vol. 130, pp. 25–37.*

Mamula et al, "Mechanisms of autoimmunity: Cryptic self polypeptides break T–cell tolerance to self–intracellular proteins", Arthritis and Rheumatism, 1992, vol. 35, No. 9, suppl., p. S38.*
Fedoseyeva et al, "Induction of T cell responses to a self–antigen following allotransplantation", Transplantation, Mar. 15, 1996, vol. 61, pp. 679–683.*
Mahi–Brown et al, "The cellular response to immunization with zona pellucida antigens", Journal of Reproductive Immunology, 1992, vol. 21, pp. 29–46.*
Bowie et al (Science, 257:1306–1310), 1990.*
Herbert et al (Dictionary of Immunology, Academic Press, London, p. 58), 1990.*
Bakker et al., "Melanocyte Lineage–specific Antigen gp100 Is Recognized by Melanoma–derived Tumor–infiltrating Lymphocytes," *The Journal of Experimental Medicine* 179:1005–1009, 1994.
Baselga et al., "Phase II Study of Weekly Intravenous Recombinant Humanized Anti–p185–$^{HER2}$ Monoclonal Antibody in Patients With HER2/neu–Overexpressing Metastatic Breast Cancer," *Journal of Clinical Oncology* 14(3):737–744, 1996.
Ben–Mahrez et al., "Circulating Antibodies Against C–MYC Oncogene Products In Sera Of Colorectal Cancer Patients," *Int. J. Cancer 46*:35–38, 1990.
Berchuck et al., "Overexpression of HER–2/neu Is Associated with Poor Survival in Advanced Epithelial Ovarian Cancer," *Cancer Research 50*:4087–4091, 1990.
Bernards et al., "Effective tumor immunotherapy directed against an oncogene–encoded product using a vaccinia virus vector," *Proc. Natl. Acad. Sci. USA 84*:6854–6858, 1987.
Cheever et al., "Specific Adoptive Therapy Of Established Leukemia With Syngeneic Lymphocytes Sequentially Immunized In Vivo And In Vitro And Nonspecifically Expanded By Culture With Interleukin 2," *The Journal Of Immunology 126*(4): 1318–1322, 1981.
Disis and Cheever, "HER–2/neu Protein: A Target for Antigen–Specific Immunotherapy of Human Cancer," *Advances in Cancer Research 71*:343–371, 1997.
Disis et al., "Existent T–Cell and Antibody Immunity to HER–2/neu Protein in Patients with Breast Cancer," *Cancer Research 54*:16–20, 1994.
Disis et al., "Immunity to the HER–2/neu oncogenic protein,". in *Vaccines Against Virally Induced Cancers*, John Wiley & Sons, Chichester, 1994, CIBA Foundation Symposium 187, pp. 198–211.

(Continued)

Primary Examiner—Karen A. Canella
(74) Attorney, Agent, or Firm—Seed IP Law Group

(57) ABSTRACT

Methods and compositions to elicit or enhance immunity in humans against self tumor antigens are disclosed. Such immunity is generated by immunization with homologous foreign proteins. Self tumor antigens include protein expression products of overexpressed human oncogenes, such as human HER-2/neu protein, and organ-specific or tissue-specific differentiation antigens, such as PAP or PSA, associated with tumor cells.

3 Claims, 16 Drawing Sheets

OTHER PUBLICATIONS

Disis et al., "Peptide–Based, but Not Whole Protein, Vaccines Elicit Immunity to HER–2/neu, an Oncogenic Self Protein," *The Journal of Immunology 156*:3151–3158, 1996.

Disis et al., "Immunization with Homologous Foreign Proteins Generates Immunity Against "Self" Tumor Antigens," *The FASEB Journal Abstracts 10*(6):p. A1470, Abstract No. 2709, 1996.

Fisk et al., "Identification of an Immunodominant Peptide of HER–2/neu Protooncogene Recognized by Ovarian Tumor-specific Cytotoxic T Lymphocyte Lines," *J. Exp. Med. 181*:2109–2117, 1995.

Gaugler et al., "Human Gene MAGE–3 Codes for an Antigen Recognized on a Melanoma by Autologous Bytolytic T Lymphocytes," *J. Exp. Med. 179*:921–930, 1994.

Gusterson et al., "Prognostic Importance of c–erbB–2 Expression in Breast Cancer," *Journal of Clinical Oncology 10*(7): 1049–1056, 1992.

Houghton, "Cancer Antigens: Immune Recognition of Self and Altered Self," *J. Exp. Med. 180*:1–4, 1994.

Katsumata et al., "Prevention of breast tumor development in vivo by downregulation of the p185$^{neu}$ receptor," *Nature Medicine I(7)*:644–648, 1995.

Kawakami et al., "Identification of the Immunodominant Peptides of the MART–1 Human Melanoma Antigen Recognized by the Majority of HLA–A2–restricted Tumor Infiltrating : Lymphocytes," *The Journal of Experimental Medicine 180*:347–352, 1994.

Kern et al., "p185$^{neu}$ Expression in Human Lung Adenocarcinomas Predicts Shortened Survival," *Cancer Research 50*:5184–5191, 1990.

Mahi–Brown et al., "The cellular immune response to immunization with zona pellucida antigens," *Journal of Reproductive Immunology 21*:29–46, 1992.

Mamula et al., "Breaking T Cell Tolerance With Foreign And Self CO–Immunogens. A Study of Autoimmune B and T Cell Epitopes of Cytochrome c," *The Journal of Immunology 149*(3):789–195, 1992.

Mamula, "The Inability to Process a Self–Peptide Allows Autoreactive T Cells to Escape Tolerance," *J. Exp. Med. 177*:567–571, 1993.

Matyas et al., "Onco Vax_PTM vaccine for prostate cancer induces immune responses to prostate specific antigen in prostate cancer patients," *Proceedings of the American Association for Cancer Research Annual Meeting 40*:576–577, 1999.

Naftzger et al., "Immune response to a differentiation antigen induced by altered antigen: A study of tumor rejection and autoimmunity," *Proc. Natl. Acad. Sci. USA 93*:14809–14814, 1996.

Nanda and Sercarz, "Induction of Anti–Self–Immunity to Cure Cancer," *Cell 82*:13–17, 1995.

Peoples et al., "Breast and ovarian cancer–specific cytotoxic T lymphocytes recognize the same HER2/neu–derived peptide," *Proc. Natl. Acad. Sci. USA 92*:432–436, 1995.

Schlichtholz et al., "The Immune Response to p53 in Breast Cancer Patients Is Directed against Immunodominant Epitopes Unrelated to the Mutational Hot Spot," *Cancer Research 52*:6380–6384, 1992.

Skinner et al., "Characterization of antigenicity and immunogenicity pattern of native and recombinant zona pellucida proteins in the white–tailed deer (*Oidocoileus virginianus*)," *Journal of Reproduction and Fertility 101*:295–303, 1994.

Slamon et al., "Human Breast Cancer: Correlation of Relapse and Survival with Amplification of the HER–2/neu Oncogene," *Science 235*:177–182, 1987.

Takahashi et al., "Antibody to ras Proteins in Patients with Colon Cancer," *Clinical Cancer Research 1*:1071–1077, 1995.

Talmadge et al.; "Preclinical evaluation of OncoVax–P a prostate cancer vaccine," *Proceedings of the American Association for Cancer Research Annual Meeting 37:* p. 477, 1996.

Yonemura et al., "Evaluation of Immunoreactivity for erB–2 Protein as a Marker of Poor Short Term Prognosis in Gastric Cancer," *Cancer Research 51*:1034–1038, 1991.

Mamula et al., "B Cells Process and Present Lupus Autoantigens that Initiate Autoimmune T Cell Responses," *J. Immun. 152*:1453–1461, 1994.

* cited by examiner

METHODS AND COMPOSITIONS TO GENERATE IMMUNITY IN HUMANS AGAINST SELF TUMOR ANTIGENS BY IMMUNIZATION WITH HOMOLOGOUS FOREIGN PROTEINS

CROSS REFERENCE TO RELATED APPLICATIONS

This application is a continuation-in-part of Ser. No. 08/625,101, filed Apr. 1, 1996, issued as U.S. Pat. No. 5,869,445, and also claims benefit to provisional application 60/048,406, filed Jun. 3,1997, now abandoned.

TECHNICAL FIELD

The present invention is generally directed toward generating immunity to self tumor antigens in humans. This invention is more particularly related to eliciting or enhancing immunity against human self tumor antigen by immunization with homologous foreign proteins.

BACKGROUND OF THE INVENTION

Despite enormous investments of financial and human resources, cancer remains one of the major causes of death. For example, cancer is the leading cause of death in women between the ages of 35 and 74. Standard approaches to treat cancer have centered around a combination of surgery, radiation and chemotherapy. Alternative approaches are needed not only to treat cancer, but also to prevent cancer.

A new generation of tumor antigens has been defined: "self proteins" (*J. Exp. Med.* 180:1–4, 1994; *Cell* 82:13–17, 1995). Self tumor antigens are proteins that are expressed by both normal cells and cancer cells. (As opposed to mutated proteins that are unique and thus cancer specific.) Self tumor antigens are typically overexpressed by the cancer cells. Certain self proteins, such as HER-2/neu and c-myc, are known to be involved in malignant transformation.

A common characteristic of malignancies is uncontrolled cell growth. Cancer cells appear to have undergone a process of transformation from the normal phenotype to a malignant phenotype capable of autonomous growth. Amplification and overexpression of somatic cell genes is considered to be a common primary event that results in the transformation of normal cells to malignant cells. The malignant phenotypic characteristics encoded by the oncogenic genes (oncogenes) are passed on during cell division to the progreny of the transformed cells.

Certain proto-oncogenes appear to be activated to a cellular oncogene through quantitative mechanisms that result from increased or deregulated expression (overexpression) of an essentially normal gene product. For example, the myc gene family has been associated with initiation and/or progression of certain human lymphomas and carcinomas, whose transforming activation is the result of quantitative mechanisms. Proto-oncogenes are believed to be essential for certain aspects of normal cellular physiology. In this regard, the HER-2/neu oncogene is a member of the tyrosine protein kinase family of oncogenes and shares a high degree of homology with the epidermal growth factor receptor. HER-2/neu presumably plays a role in cell growth and/or differentiation. HER-2/neu appears to induce malignancies through quantitative mechanisms that result from increased or deregulated expression of an essentially normal gene product.

HER-2/neu (p185) is the protein product of the HER-2/neu oncogene. The HER-2/neu gene is amplified and the HER-2/neu protein is overexpressed in a variety of cancers including breast, ovarian, colon, lung and prostate cancer. HER-2/neu is related to malignant transformation. It is found in 50%–60% of ductal in situ carcinoma and 20%–40% of all breast cancers, as well as a substantial fraction of adenocarcinomas arising in the ovaries, prostate, colon and lung. HER-2/neu is intimately associated not only with the malignant phenotype, but also with the aggressiveness of the malignancy, being found in one-fourth of all invasive breast cancers. HER-2/neu overexpression is correlated with a poor prognosis in both breast and ovarian cancer. HER-2/neu is a transmembrane protein with a relative molecular mass of 185 kd that is approximately 1255 amino acids (aa) in length. It has an extracellular binding domain (ECD) of approximately 645 aa, with 40% homology to epidermal growth factor receptor (EGFR), a highly hydrophobic transmembrane anchor domain (TMD), and a carboxyterminal intracellular domain (ICD) of approximately 580 aa with 80% homology to EGFR.

Thus, HER-2/neu and c-myc, which are normal proteins found to be associated with malignant transformation when overexpressed, are examples of self tumor antigens. Other examples of self tumor proteins are those expressed by melanoma cells as melanocyte differentiation antigens, such as gp100, MAGE and MART-1. Self tumor proteins have been found to stimulate an immune response in some patients whose cancers express those proteins (e.g., *J. Exp. Med.* 179:921–930, 1994; 179:1005–1009, 1994; and 180:347–352, 1994). However, despite the presence of a detectable immune response to self tumor antigens in some patients, immunologic tolerance exists and represents a potential barrier to effectively vaccinating against tumor antigens. For example, rats vaccinated with either purified rat neu protein or rat neu extracellular domain (ECD) expressed by vaccinia virus do not develop rat neu specific immunity (*Proc. Natl. Acad. Sci. USA* 84:6854–6858, 1987). Tolerance can be circumvented in the rat, however, by immunization with peptides derived from the rat neu protein sequence. Nevertheless, the use of peptides may be problematic as they are thought of as weak immunogens and HLA restriction may limit usefulness (e.g., by preventing the use of a single peptide for all patients). An ideal vaccine strategy targeting a self tumor antigen would be one in which vigorous immunity could be elicited with one vaccine formulation for all patients.

Due to the difficulties in the current approaches to treatment and prevention of cancer, there is a need in the art for improved methods and compositions. The present invention fulfills this need, and further provides other related advantages.

SUMMARY OF THE INVENTION

Briefly stated, the present invention provides methods and compositions for eliciting or enhancing an immune response to a human self tumor antigen. The methods and compositions may be used on a one-time basis or on a periodic basis. The method comprises immunizing a human being with a foreign protein homologous to the antigen or with a foreign peptide homologous to a portion of the antigen.

In one embodiment of the method, the human self tumor antigen is a protein expression product of an overexpressed human oncogene. In a preferred embodiment, the antigen is human HER-2/neu protein. In another embodiment, the portion of the antigen is a portion of a protein expression product of an overexpressed human oncogene. In a preferred embodiment, the portion is a portion of human HER-2/neu protein. In a particularly preferred embodiment, the portion includes the intracellular domain of human HER-2/neu protein.

In another embodiment of the method, the human self tumor antigen or antigen portion is an organ-specific or tissue-specific differentiation antigen associated with tumor cells or a portion of the antigen. In a preferred embodiment, the human self tumor antigen or antigen portion is an antigen, or portion thereof, associated with prostate cancer. In a particularly preferred embodiment, the antigen is PAP. In another particularly preferred embodiment, the antigen is PSA.

In any embodiment of the invention, the foreign protein or foreign peptide is optionally in a pharmaceutically accepted carrier or diluent. Similarly, in any embodiment, an adjuvant may be additionally included.

These and other aspects of the present invention will become evident upon reference to the following detailed description and attached drawings.

DETAILED DESCRIPTION OF THE INVENTION

Figure 1A:
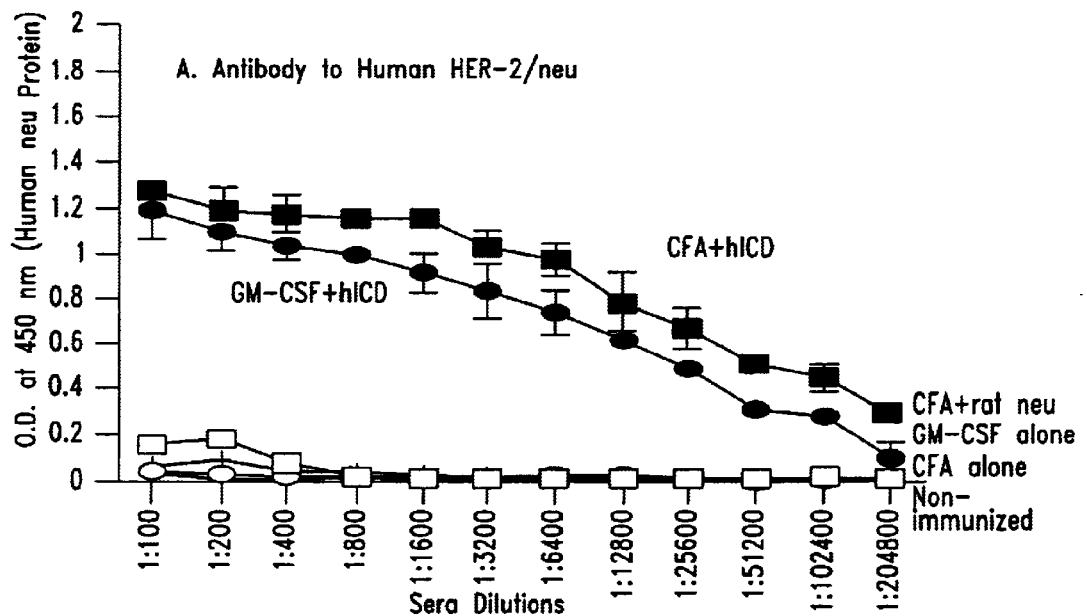
FIGS. 1A–B show that rats immunized with intracellular domain of the human HER-2/neu protein (hICD) develop high titer human and rat neu specific antibodies. This figure represents data collected from 2 separate experiments with 8 experimental animals in each group. The greatest inter assay standard deviation, at the most concentrated control sera dilution, was 0.12 O.D. Three control animals that were not immunized are shown as an example of a naive rat response to human HER-2/neu and rat neu proteins. (A) Human HER-2/neu specific antibody responses were determined by ELISA. Results are depicted as the mean and standard deviation of the antibody response of each experimental group at each sera dilution. (B) Rat neu specific antibody responses were determined by ELISA. Results are depicted as the mean and standard deviation of the antibody response of each experimental group at each sera dilution.

As noted above, the present invention is directed toward methods and compositions to elicit or enhance immunity against human self tumor antigens. Because a self tumor antigen is a self protein (i.e., a protein produced normally by an individual and not unique to a tumor), immunologic tolerance exists and represents a potential barrier to effectively vaccinating against such tumor antigens. The present invention overcomes immunologic tolerance by immunizing an individual with a protein or peptide that is foreign (i.e., not identical to that in the individual) but nevertheless homologous to an individual's self tumor antigen or portion thereof.

As used herein, a "self tumor antigen" is a protein (including glycoproteins, lipoproteins, phosphoproteins, etc., or their amino acid sequences only) that is associated with a tumor in an individual, but has an amino acid sequence that is identical to a protein which is produced by the individual in the absence of the tumor. A variety of tumor antigens are self tumor antigens, and include the expression products of oncogenes. Certain oncogenes appear to induce malignancies through quantitative mechanisms that result from increased or deregulated expression of an essentially normal gene product. Self tumor antigens also include organ-specific and tissue-specific differentiation antigens associated with malignant cells. Self tumor antigens are associated with a variety of cancers including breast, ovarian, colon, lung and prostate.

Examples of self-tumor antigens that are the protein product of an oncogene that is amplified such that the protein is overexpressed by the tumor, include human HER-2/neu and the members of the myc family. Within the present invention, human HER-2/neu is a preferred self tumor antigen. An example of an organ that possesses organ-specific self tumor antigens is the prostate. Within the present invention, human prostate specific antigen (PSA) and human prostatic acid phosphatase (PAP) are preferred self tumor antigens.

The present invention discloses surprisingly that immunization of a human with a foreign protein that is homologous (i.e., not identical) to a human self tumor antigen will result in the development of significant antibody and T cell responses to the self tumor antigens, including substantial reactivity to epitopes that are identical between the foreign protein and the self tumor antigen. As used herein, a "foreign protein homologous to a human self tumor antigen" means a protein that is homologous but not identical in entire amino acid sequence to a human self tumor antigen. Generally, a foreign protein will possess at least about 50% sequence homology to the self tumor antigen targeted. Sequence homology means either identical amino acids at the same positions in the sequence (i.e., sequence identity), or conservative substitutions of amino acids at the same positions in the sequence. Conservative substitutions are well known in the art. Examples are isoleucine for leucine, valine for alanine, glutamic acid for aspartic acid, threonine for serine, etc. Typically, a foreign protein will possess about 55%, 60%, 65%, 70%, 75%, 80%, 85%, 90%, 95% or 99% sequence homology. Preferred foreign proteins are those which are highly homologous, e.g., with 90%, 91%, 92%, 93%, 94%, 95%, 96%, 97%, 98%, 99%, or greater than 99% but less than 100% sequence homology. Particularly preferred foreign proteins are those wherein the aforementioned sequence homology percents each represent percent sequence identity.

Within the present invention, a foreign peptide may be used in place of, or in combination with, a foreign protein. Additionally, a foreign protein or peptide or both may be used in combination with a human self tumor antigen. Where two or more proteins/peptides are used in combination, they may be administered simultaneously or sequentially. As used herein, a "foreign peptide homologous to a portion of a human self tumor antigen" means a peptide that is homologous but not identical in its entire amino acid sequence to a portion of the amino acid sequence of a human self tumor antigen. The above discussion regarding sequence homology, percentages of sequence homology, preferred sequence homology percentages, preferred sequence identity percentages, etc., is applicable to foreign peptides and is incorporated by reference.

It will be evident to one of ordinary skill in the art that a foreign protein or foreign peptide for the present invention may be obtained in a variety of ways. For example a foreign protein or peptide may be purchased where available commercially. A foreign protein may be isolated from a non-human source. A foreign protein may be produced using a nucleic acid sequence encoding the foreign protein in combination with standard molecular biology methodologies. Alternatively, a foreign protein may be produced by standard molecular biology methodologies using a nucleic acid sequence which is a modified form of that encoding a self tumor antigen. For example, a nucleic acid sequence may be modified using random or site-specific mutagenesis. A foreign peptide may be similarly produced, or may be chemically synthesized (by manual or automated procedures) if its length is within the range appropriate for such methodologies. Automated peptide synthesizers are commercially available (e.g., Perkin Elmer-Applied Biosystems Division, Foster City, Calif.). Commercial services are available to obtain peptides of a desired sequence (e.g., Multiple Peptide Systems, San Diego, Calif.).

Another way to generate a foreign protein, or foreign peptide, for the present invention is to link a self tumor antigen, or portion thereof, to one or more essential differences in amino acid sequence between a self and a homologous foreign protein. An essential difference between amino acid sequences is a non-conservative substitution of an amino acid at the same position for the two sequences. Examples of essential differences are a charged versus a non-charged amino acid, an acidic versus a basic amino acid, etc. Such a foreign protein may be produced, for example, by fusion protein methodologies (nucleic acid sequences encoding desired portions of self and foreign proteins are combined) or site-specific mutagenesis (of nucleic acid sequence encoding self tumor protein to incorporate essential differences).

A variety of organisms produce proteins that qualify as foreign proteins. Such proteins (or peptides therefrom) may be used directly in the present invention or the information concerning their amino acid sequence (or sequence differences with human self tumor antigen) used to generate foreign proteins or foreign peptides. An example of an organism that produces foreign proteins homologous to human self tumor antigens is a rat. For example, the rat neu protein is homologous but not identical in entire amino acid sequence of human HER-2/neu protein. Thus, the rat neu protein, or a peptide thereof, may be used as a foreign protein or peptide in the present invention to immunize a human being.

Immunization of an individual with a foreign protein or peptide (e.g., as a vaccine) may include a pharmaceutically suitable carrier or diluent, such as physiological saline or sera. It will be recognized by one or ordinary skill in the art that the composition should be prepared in sterile form. Typically, about 0.01 $\mu$g/kg to about 100 mg/kg body weight will be administered by the intradermal, subcutaneous or intravenous route. A preferred dosage is about 1 $\mu$g/kg to about 1 mg/kg, with about 5 $\mu$g/kg to about 200 $\mu$g/kg particularly preferred. It will be evident to those skilled in the art that the number and frequency of administration will be dependent upon the response of the patient. It may be desirable to administer the foreign protein or peptide repetitively. It will be evident to one of ordinary skill in the art that more than one foreign protein or peptide may be administered, either simultaneously or sequentially.

In addition to the foreign protein or peptide (which functions as an antigen), it may be desirable to include other components with the foreign protein or peptide, such as a vehicle for antigen delivery and immunostimulatory substances designed to enhance the protein's immunogenicity. Examples of vehicles for antigen delivery include aluminum salts, water-in-oil emulsions, biodegradable oil vehicles, oil-in-water emulsions, biodegradable microcapsules, and liposomes. Examples of immunostimulatory substances (adjuvants) include N-acetylmuramyl-L-alanine-D-isoglutamine (MDP), lipopoly-saccharides (LPS), glucan, IL-12, GM-CSF, gamma interferon and IL-15. When a peptide is used, it may be desirable to couple the peptide hapten to a carrier substance, such as keyhole limpet hemocyanin.

Immunization by the methods of the present invention results in the elicitation or enhancement of an immune response to a human self tumor antigen. Such an immunization may be performed for one of a variety of purposes. For example, it may be desired to elicit or enhance an immune response as a preventive measure to prevent tumor occurrence or recurrence, or as a therapy to arrest tumor growth or eradicate existing tumors or to prolong the survival time. Eradicating tumor growth is based on stimulating an individual's immune system to induce a sustained destructive autoimmune response to cancer cells expressing the self tumor antigen. For example, eradicating prostate cancer cells is based on immunizing with a foreign protein or peptide to differentiation antigens expressed exclusively by the prostate gland in order to induce a sustained destructive autoimmune prostatitis. However, as described above, eliciting or enhancing an immune response to a human self tumor antigen can be useful even absent eradication of tumors.

The following examples are offered by way of illustration and not by way of limitation.

EXAMPLES

Example 1

HER-2/neu Immunization

A. Materials and Methods

1. Animals: Rats used in this study were Fischer strain 344 (CDF (F-344)/CrlBR) (Charles River Laboratories, Portage Mich.). Animals were maintained at the University of Washington Animal facilities under specific pathogen free conditions and routinely used for experimental studies between 3 and 4 months of age. Pathologic evaluation of rat tissues was performed by Dr. D. Liggitt, University of Washington, Department of Comparative Medicine.

2. Neu Proteins. Rat neu protein was purified using immunoaffinity column purification techniques. Briefly, a lysate preparation of a rat neu overexpressing cell line, DHFRG8 (ATCC, Rockville Md.), was incubated overnight at 4° C. on a prepared immunoaffinity Affigel-10 column (BioRad, Hercules, Calif.). $20 \times 10^7$ cells were used to generate the lysate preparation (Disis et al., J. Immunol. 156:315–13158, 1996). The Affigel-10 was coupled a rat neu specific antibody, 7.16.4 (kindly supplied by Dr. Mark Greene). After incubation with lysate, the column was washed three times, twice with PBS and once with 1 M NaCl. The rat neu protein was eluted with a buffer: pH 2.5, 0.05 M glycine, 0.15 M NaCl, and 0.1% Triton-X and the eluent was immediately brought back to neutral pH with 1M Tris HCl. Pooled protein fractions were dialyzed against PBS. After dialysis, the protein was concentrated by centrifugation (Centricon-100, Amicon, Beverly, Mass.). The rat neu protein was sterile filtered (Nalgene, Rochester, N.Y.). Protein purity was verified by both protein staining and Western blot (Disis et al., ibid.). Purified protein was quantified (Bio-Rad Protein Kit). Recombinant human and rat ICD proteins were kindly provided by Dr. Kenneth Grabstein (Corixa Corp., Seattle, Wash.).

3. Immunization: Rats were immunized recombinant human HER-2/neu intracellular domain protein (hICD) (50 µg), or immunoaffinity column purified rat neu protein (50 µg). Proteins were administered with either CFA (Sigma ImmunoChemicals, St. Louis, Mo.) or murine GM-CSF 5 µg (Immunex Corp., Seattle, Wash.) as adjuvants. Control groups received adjuvant alone. Inoculations with GM-CSF were given id and inoculations with CFA were administered sq. Animals underwent 2 immunizations each 14–16 days apart. 18–20 days after the second immunization animals were assessed for immunologic response. DTH responses to rat neu protein were assessed. Sera, spleens and draining lymph nodes were harvested from immunized animals. Experiments included 4 animals/experimental group. Data shown here was derived from two separate immunization experiments for each group performed more than 2 months apart.

4. Cell Lines: Two cell lines were used as a source of neu proteins. SKBR3, a human breast cancer cell line that is a marked overexpressor of HER-2/neu (American Type Culture Collection, Rockville, Md.), was maintained in culture in 10% fetal bovine serum (FBS) (Gemini Bioproducts, Inc., Calabasas, Calif.) and RPMI. DHFRG8, an NIH/3T3 cell line cotransfected with c-neu-p and pSV2-DHFR (American Type Culture Collection, Rockville, Md.), was used as a source of non-transforming rat neu protein. This cell line was maintained in 10% FBS and Dulbecco's modified Eagle's medium with 4.5g/L glucose. DHFRG8 cells were passaged through the same medium supplemented with 0.3 µM methotrexate at every third passage to maintain the neu transfectant.

5. ELISA for rat neu and human HER-2/neu specific antibody responses: 96 well Immulon 4 plates (Baxter SP, Redmond, Wash.: Dynatech Laboratories) were incubated overnight at 4° C. with either a rat neu specific antibody (c-neu-4, Oncogene Science) or a human HER-2/neu specific antibody (520-C9, a kind gift of Dr. David Ring) at a concentration of 10 µg antibody per ml in carbonate buffer. After incubation, all wells were blocked with PBS and 1% bovine serum albumin (BSA) (Sigma Chemical Co., St. Louis, Mo.), 100 µl/well for 4 hours at room temperature. The plate was washed with PBS/0.5% Tween and protein was added. Rows of wells were coated with alternating PBS/1%BSA and DHFR-G8 lysate (rat neu) or SKBR3 lysate (human HER-2/neu) ($10^8$ cells/20 ml PBS), 50 µl/well, overnight at 4° C. After washing, the plate was incubated with rat sera at the varying dilutions in PBS/1% BSA and incubated 1 hour at room temperature. Sheep anti-rat Ig horseradish peroxidase (HRP) was added to the wells at a 1:5000 dilution in PBS/1%BSA and incubated for 45 minutes at room temperature (Amersham Co.). Following the final wash, TMB (Kirkegaard and Perry Laboratories, Gaithersburg, Md.) developing reagent was added. The optical density was read at 450 nm. The OD of each serum dilution was calculated as the OD of the neu coated wells minus the OD of the PBS/1%BSA coated wells.

Antigen specificity was confirmed by analyzing experimental sera for antibody responses to ova albumin in an ELISA. In these analysis, plates were incubated overnight at 4° C. with purified ova albumin protein at 10 µg/ml concentration in carbonate buffer alternating with rows of buffer alone. Antibody evaluation proceeded as described above.

6. ELISA for peptide epitope analysis: 96 well Immulon 4 plates (Dynatech Laboratories) were incubated overnight at 4° C. with neu peptides at a concentration of 10 µg/well diluted in PBS alternating with rows of PBS/1%BSA. The peptides constructed were 15–18 amino acids in length and were derived from the amino acid sequence of the rat neu protein. Some peptides were located in areas of 100% homology between rat neu and human HER-2/neu. The peptide coated plate was incubated with rat sera diluted 1:50 and 1:100 for 1 hour at room temperature. Sheep anti-rat HRP was added to the wells at a 1:5000 dilution in PBS/1%BSA and incubated for 45 minutes at room temperature. Following the final wash, the TMB developing reagent was added. The optical density was read at 450 nm. The OD of each serum dilution was calculated as the OD of the peptide coated wells minus the OD of the PBS/1%BSA coated wells.

7. Delayed Type Hypersensitivity (DTH) responses: 18 days after the final inoculation baseline ear thickness was measured in each animal using a dual thickness gauge (Mitutoyo Corporation, Japan). Immediately following the baseline measurement, the left ear was treated epicutaneously with a carrier solvent consisting of a 1:1 mix of acetone and dibutyl pthalate. 10 µl of the carrier solvent was applied to the front of the ear and 10 µl was applied to the back of the ear. The right ear of each animal was treated with the carrier solvent and antigen with 10 µl of the carrier diluted antigen mix applied to the front of the ear and 10 µl applied to the back of the ear. Animals were tested with 1 µg/ml of purified rat neu protein. DTH response as a measure of ear thickness was measured at 48 hours and calculated as the difference in the thickness of the experimental ear compared to control.

8. T cell proliferation assays: For analysis of neu protein specific responses, immune spleen cells were harvested by mechanical disruption and passage through wire mesh and washed. $2 \times 10^5$ spleen or $1 \times 10^5$ lymph node cells/well were plated into 96-well round bottom microtiter plates (Corning, Corning, N.Y.) with 6 replicates per experimental group. The media used consisted of EHAA 120 (Biofluids) with L-glutamine, penicillin/streptomycin, 2-mercaptoethanol, and 5% FBS. In initial experiments, cells were incubated with 1 µg/ml of the various proteins. Subsequent experiments evaluated increasing concentrations of experimental proteins, recombinant human HER-2/neu ICD and recombinant rat neu ICD, ranging from 0.5 to 2.0 µg/ml. After 4 days, wells were pulsed with 1 µCi of [3H] thymidine for 6–8 hours and counted. Data is expressed as a stimulation index which is defined as the mean of the experimental wells divided by the mean of the control wells (no antigen). Ova albumin was used as a negative control antigen for proliferation in all assays at a 1 µg/ml concentration.

B. Results

1. Rats immunized with hICD develop high titer human and rat neu specific antibodies. Previous studies demonstrated that rats, immunized with rat neu protein, do not develop immune responses to rat neu (Bernards et al., *Proc. Natl. Acad. Sci. USA* 84:6854–6858, 1987). Animals are presumed tolerant to this "self" protein. For the current study, rats were given a priming immunization and a boost immunization with hICD with either GM-CSF or CFA as an adjuvant. All rats immunized with hICD developed significant antibody responses specific for human HER-2/neu protein, with titers greater than 1:200,000 (FIG. 1A). By marked contrast, rats immunized with rat neu protein did not develop human neu specific antibodies. Ova albumin was used as a negative control protein. No sera tested was positive for antibodies to ova.

Figure 1B:
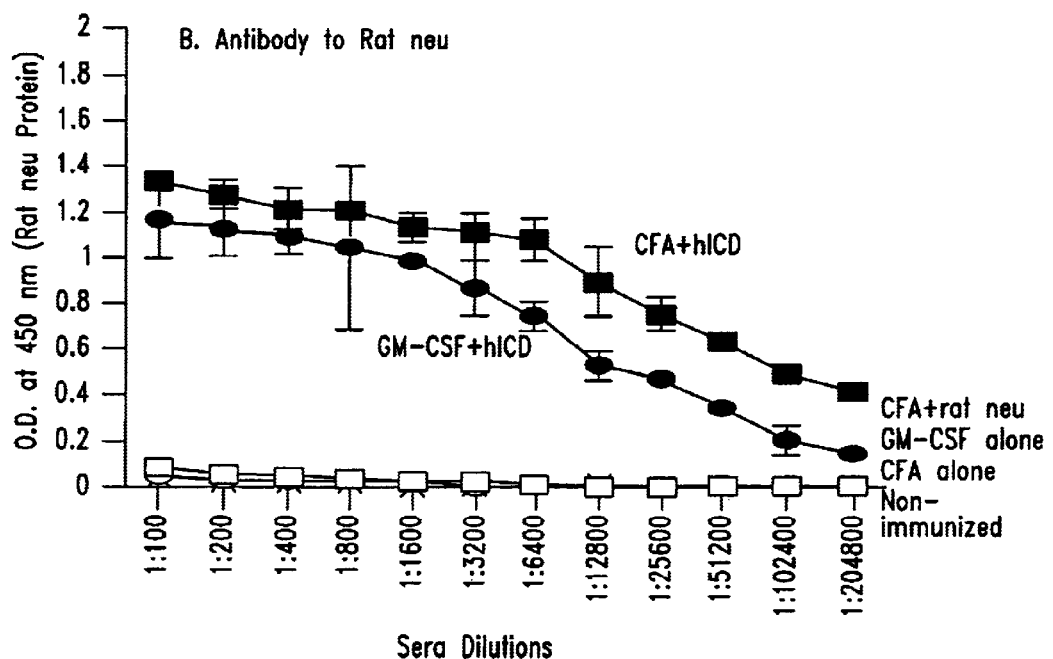

Human HER-2/neu ICD is 92% homologous to rat neu ICD at the amino acid level. Analysis was performed to discern whether the human HER-2/neu specific antibodies were cross-reactive with rat neu. Rats immunized with hICD with either GM-CSF or CFA as an adjuvant had high titer antibody responses specific for rat neu (FIG. 1B). The magnitude of the rat neu specific antibody responses was nearly identical to that of the human HER-2/neu specific response.

Figure 2:
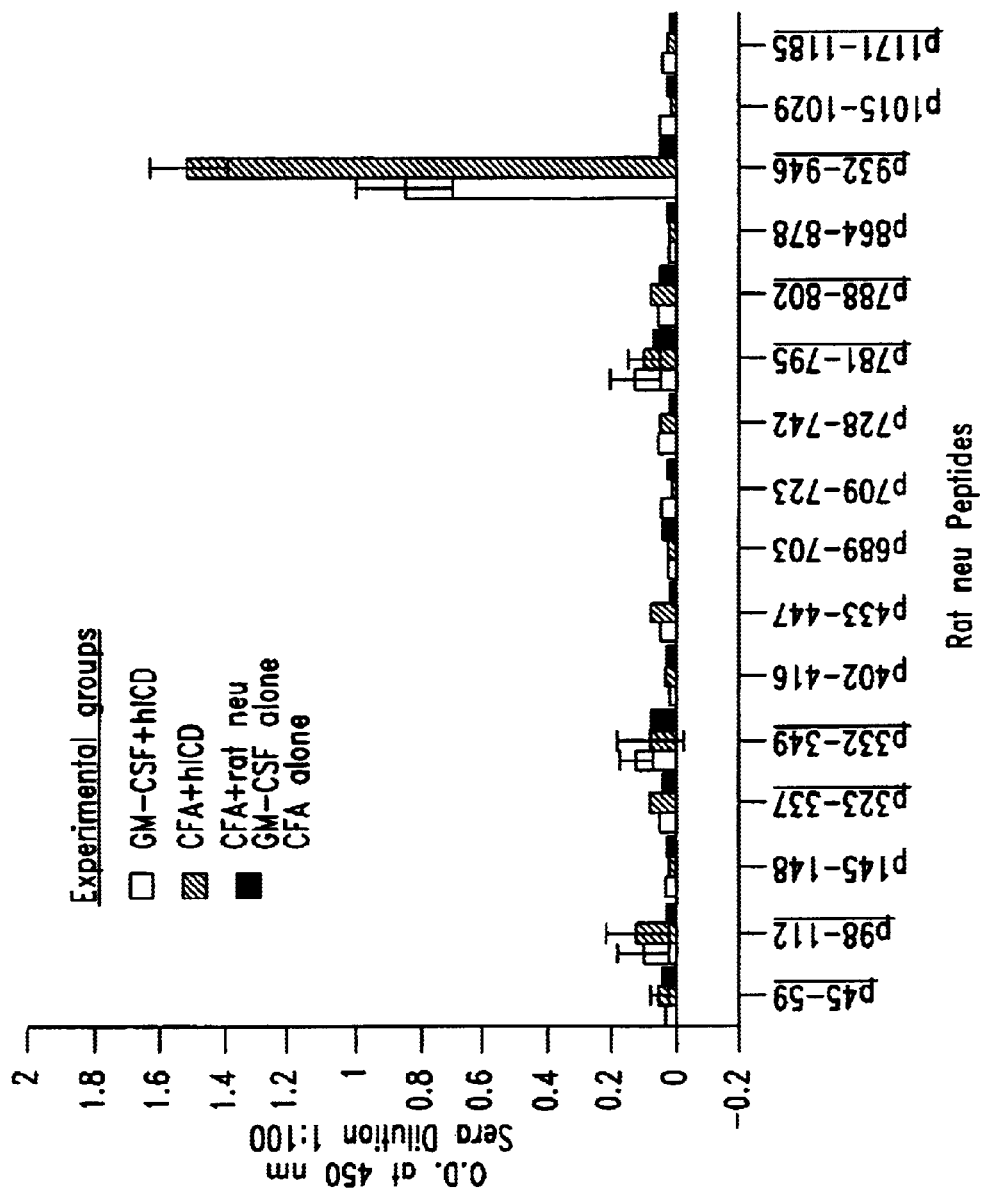
FIG. 2 shows that human HER-2/neu and rat neu specific antibodies, generated by immunizing with hICD, are specific for an intracellular domain epitope with 100% homology between rat and human neu. Sera derived from animals in each experimental group were evaluated in ELISA for antibody response to 16 peptides derived from the amino acid sequence of the rat neu protein structure. Eight of the sixteen peptides were derived from sections of the rat neu protein that were 100% homologous with human neu. These peptides are underlined. This figure represents data collected from 2 separate experiments with 8 experimental animals in each group. Results are depicted as the mean and standard deviation of the antibody response of each experimental group at a sea dilution of 1:100.

Human HER-2/neu and rat neu specific antibodies, generated by immunizing with hICD, are specific for an intracellular domain epitope with 100% homology between rat and human neu. Epitope mapping was done with a series of synthetic peptides (n=16) derived from the amino acid sequence of the rat neu protein. Both intracellular and extracellular peptides were included. Eight of the peptides were derived from region of the rat neu protein that were 100% homologous with human HER-2/neu protein. The dominant response detected was to an ICD peptide epitope, p932–946 (FIG. 2). The amino acid sequence of this peptide is identical between rat and human.

Figure 3:
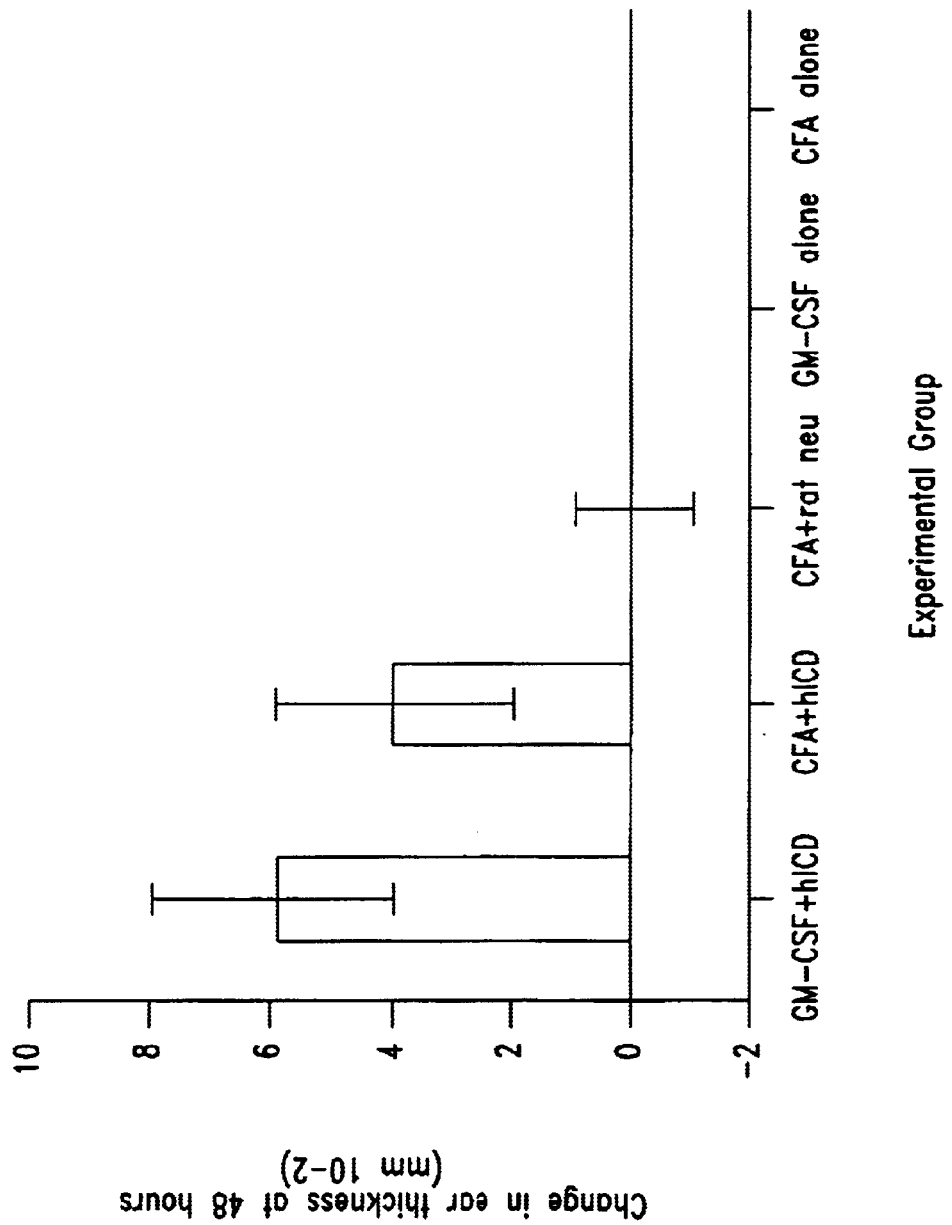
FIG. 3 shows that rats immunized with hICD develop DTH responses to rat neu protein. Animals were tested for DTH responses to rat neu protein 18–20 days after the last of two immunizations with hICD. The change in ear thickness is defined as the width of the experimental ear exposed to antigen in solvent minus the width of the control ear exposed to carrier solvent alone. Data is the mean and standard deviation of 4 animals in each experimental group.

2. Rats immunized with hICD develop DTH responses to rat neu protein. The conditions for circumventing T cell tolerance may be more stringent than those needed to break B cell tolerance. Key for a successful cancer vaccine targeting a "self" tumor antigen is the ability to generate significant T cell immunity. DTH responses were used to initially evaluate for the presence of the T cell responses to neu in rats immunized with HER-2/neu. HER-2/neu specific DTH responses were detected in animals who received hICD in GM-CSF or CFA (FIG. 3). The responses were cross-reactive to rat neu protein. DTH was not detected in animals immunized with rat neu protein or with adjuvants alone.

Figure 4A:
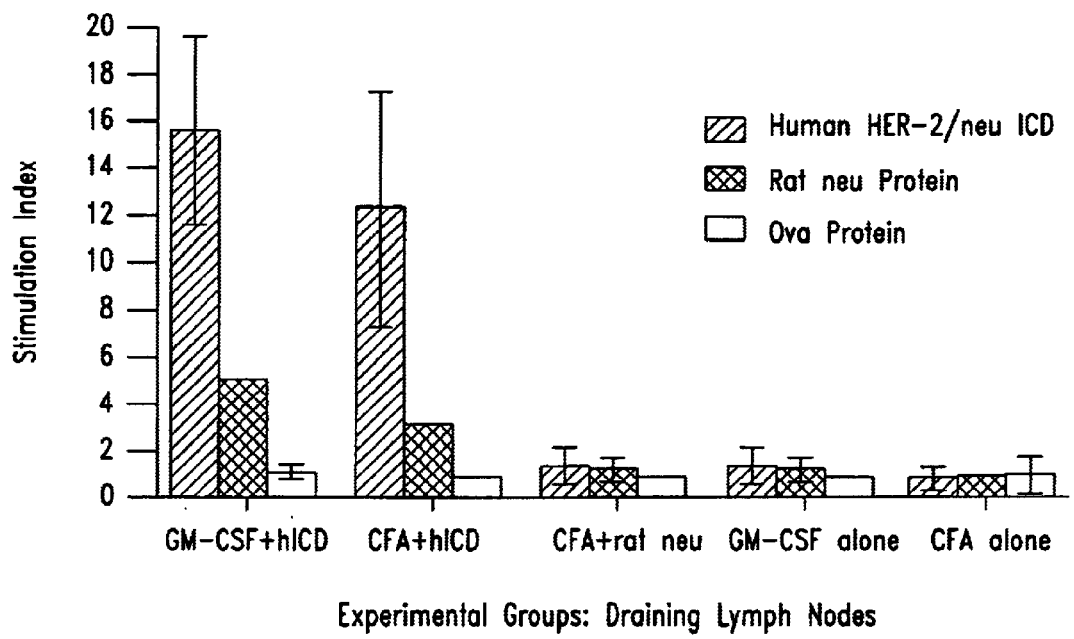
FIGS. 4A–B show that immunization of rats with hICD elicits detectable T cell responses specific for both human and rat neu protein. (A) T cells ($1 \times 10^5$) derived from draining lymph nodes of experimental rats were incubated with 1 $\mu$g/ml of recombinant hICD, purified rat neu protein or ova albumin as an irrelevant control protein. Proliferative responses were assayed after 4 days of culture in 6 well replicates. The data is expressed as a stimulation index which is the mean of the experimental wells divided by the mean of the control (no antigen) wells. Background proliferation of lymph node cells in media with no antigen ranged from 3275+/−790 to 9325+/−945 cpm. (B) T cells derived from spleens of immunized rats were assayed in the same fashion as the lymph node cells. Background proliferation ranged from 4795+/−725 to 8570+/−873 cpm. Data is the mean and standard deviation of 4 animals in each experimental group.
Figure 4B:
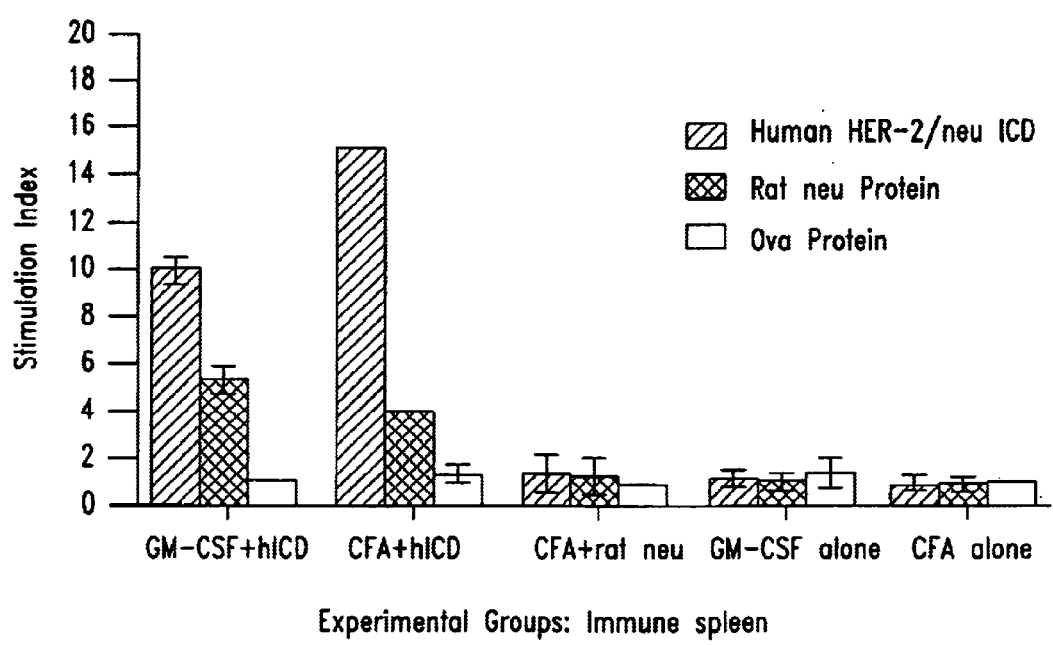

3. Immunization of rats with hICD elicits detectable T cell responses specific for both human and rat neu protein. T cell proliferative responses were evaluated in rats immunized with hICD plus either GM-CSF or CFA. T cell responses to hICD protein were detected from lymph nodes draining the inoculation site (FIG. 4A) and spleen (FIG. 4B). T cell responses to rat neu protein were also detected, although at a lower magnitude than the hICD response. There was no evidence of response to an irrelevant protein, ova albumin. Animals immunized with rat neu protein with adjuvants or adjuvants alone did not have a detectable T cell response to either hICD or rat neu protein.

Figure 5:
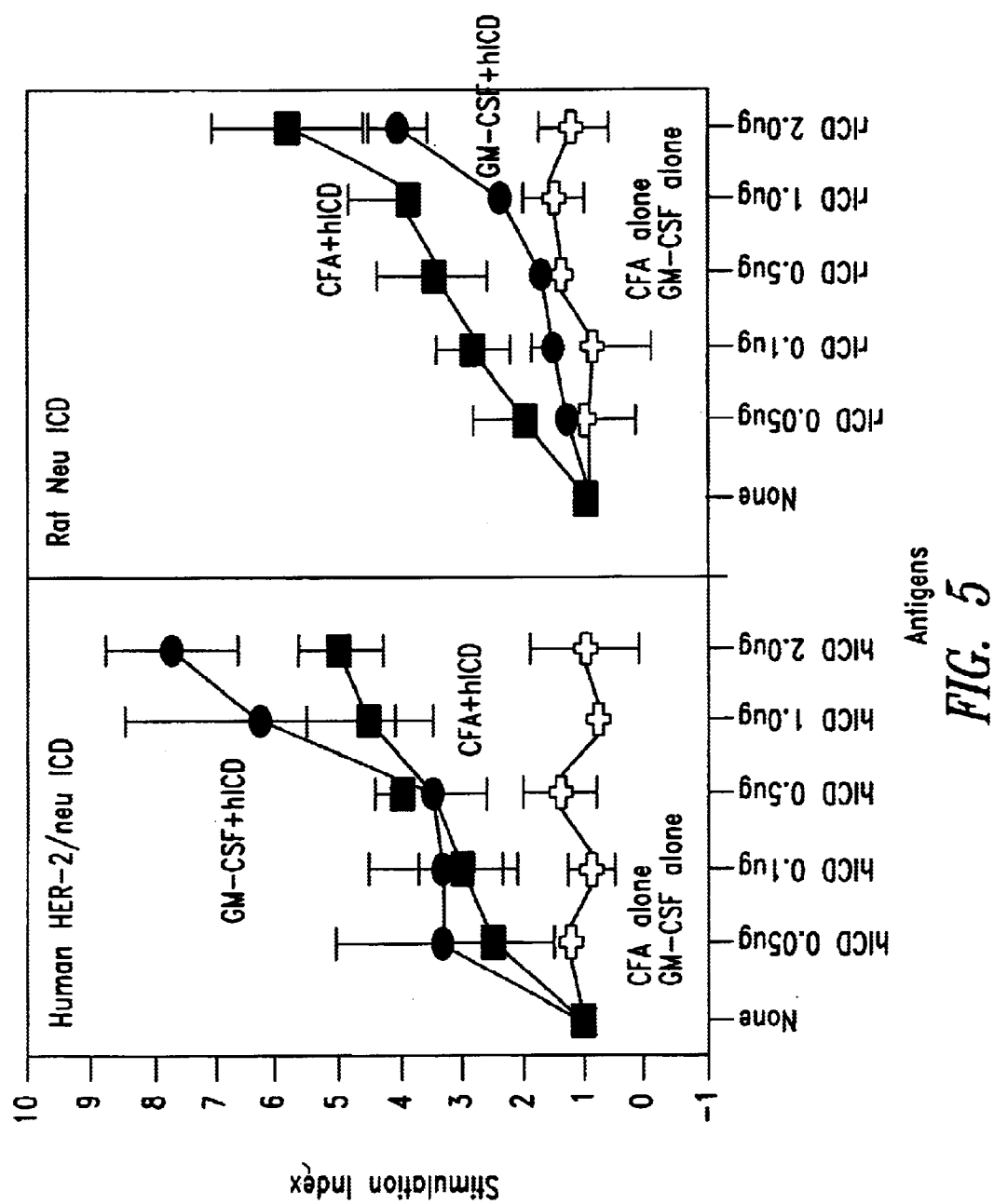
FIG. 5 shows that rats immunized with hICD developed proliferative responses to both human and rat ICD protein in a dose dependent fashion. T cells ($2 \times 10^5$) derived from spleens of immunized rats were incubated with increasing concentrations of recombinant hICD or recombinant rat ICD neu proteins. Proliferative responses were assayed after 4 days culture in 6 well replicates. The data is expressed in terms of a stimulation index which is the mean of the experimental wells divided by the mean of the control (no antigen) wells. Background proliferation of lymph node cells in media with no antigen ranged from 835+/−84 to 11,584+/−1450 cpm. None of the animals tested had an S.I. to ova albumin greater than 1.5 (data not shown). Data is expressed as the mean and standard deviation of 4 animals in each experimental group. This data represents a separate experiment from animals immunized in the experiment summarized in FIG. 3.
Figure 6:
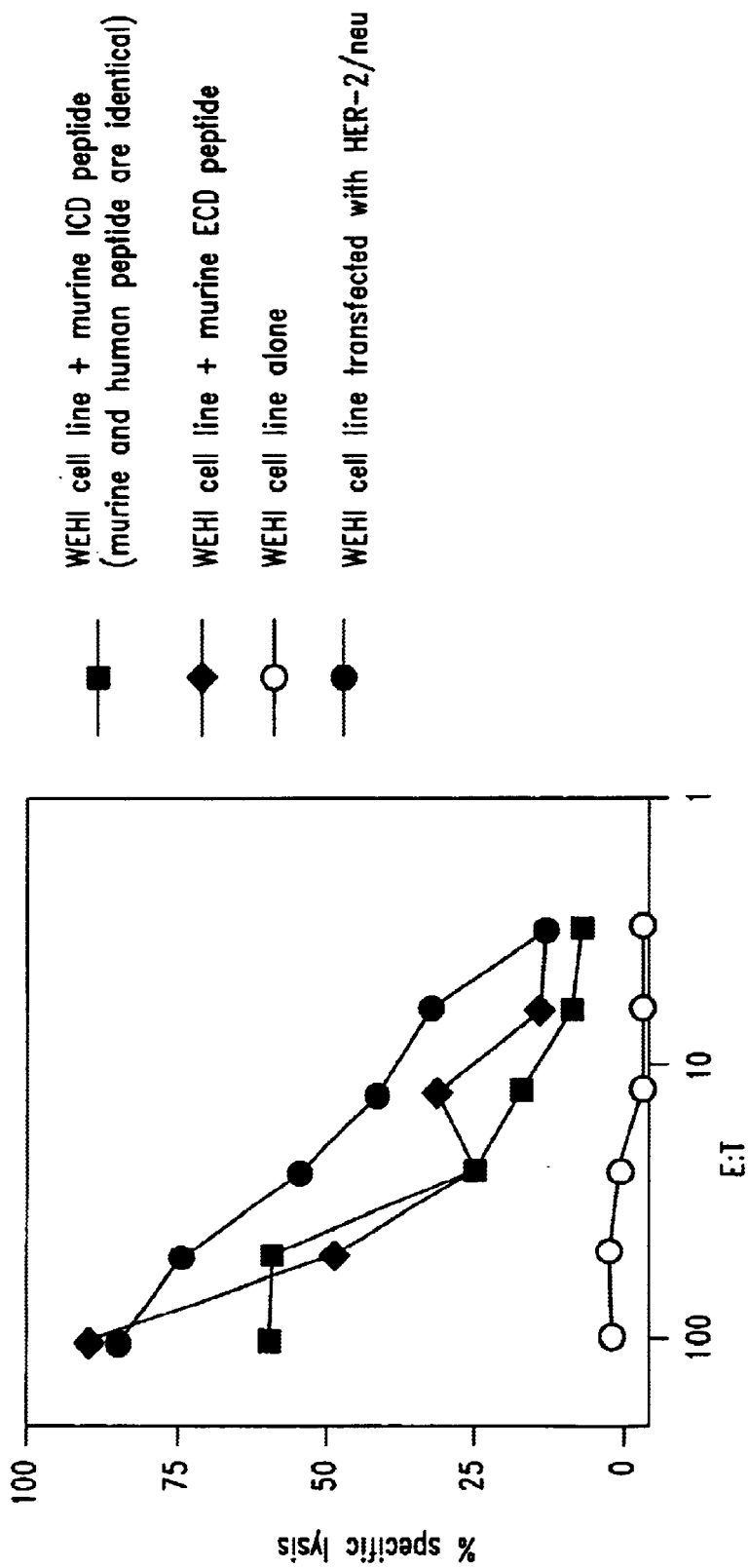
FIG. 6 shows that CTL lines generated by immunization with human HER-2/neu DNA recognized both naturally processed human HER-2/neu epitopes as well as murine HER-2/neu epitopes.

Rats immunized with hICD developed significant proliferative responses to both human and rat ICD protein in a dose dependent fashion (FIG. 5). The magnitude of the T cell immune responses directed against rat or human neu protein was similar in rats immunized with hICD plus CFA at the greatest concentration of antigen tested (2.0 µg). The magnitude of the T cell response against rat was less than the response to human in rats immunized with hICD plus GM-CSF at all concentrations. However, the possibility exists that the responses would become more equivalent with additional boosting.

Biopsies of skin, liver, lung, gastrointestinal tract, kidney and heart were obtained from immunized animals and evaluated for histopathologic evidence of autoimmunity. There was no evidence of autoimmune pathology in these tissues which express basal levels of rat neu protein.

4. CTL lines generated by immunization with human HER-2/neu DNA recognized both naturally processed human HER-2/neu epitopes as well as murine HER-2/neu epitopes. BALB/c mice were immunized with human HER-2/neu DNA (100 Ug x3 id.). Spleen cells were cultured for 5 days with WEHI cell line transfected with HER-2/neu as stimulator cells. CTL activity was assessed in a standard 4 hour chromium release assay on day 5. The targets included WEHI alone, WEHI transfected with HER-2/neu, WEHI incubated with the HER-2/neu intracellular domain (ICD) peptide denoted p780–788 (identical in humans and mice) or with WEHI incubated with the HER-2/neu murine extracellular domain peptide denoted p63–71.

Figure 7A:
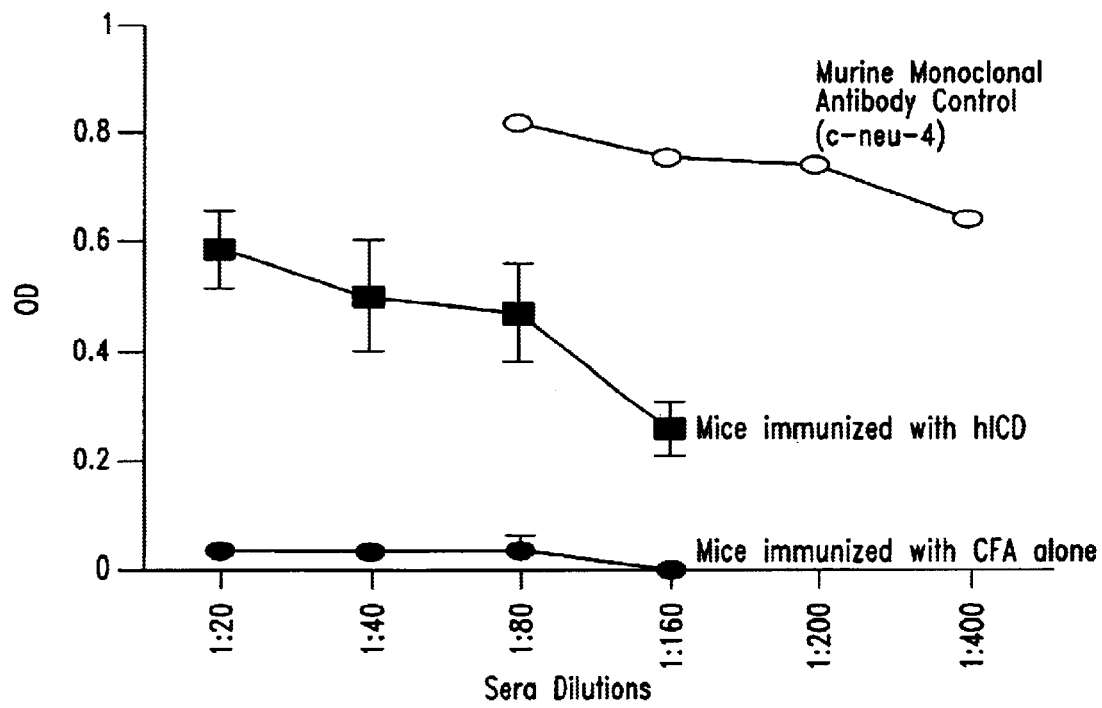
FIGS. 7A–B show that mice immunized with hICD develop antibodies (A) and T cells (B) specific for rat neu.
Figure 7B:
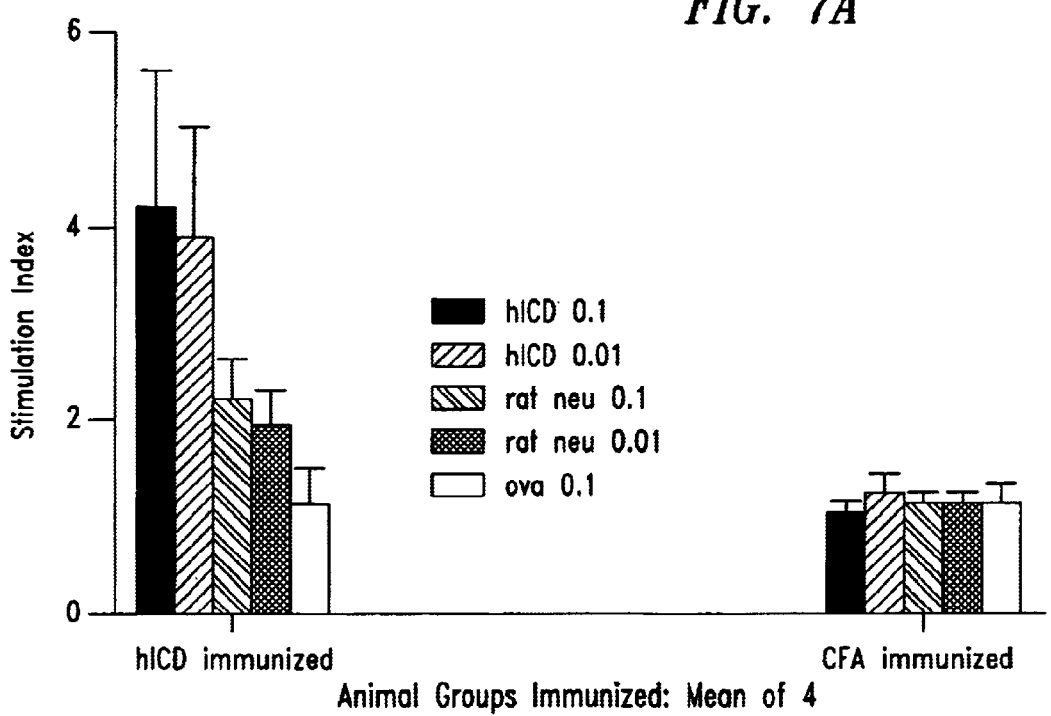

5. Mice immunized with hICD develop antibodies and T cells specific for rat neu. FIGS. 7A–B show the generation of immunity in another self model—the neu transgenic mouse. This is a mouse which has rat neu on an MMTV promoter and develops breast cancer mediated by overexpression of rat neu in mid to late life. In this mouse, rat neu is a self protein. FIG. 7A shows that if this mouse is immunized with human ICD, a rat neu antibody response is obtained. FIG. 7B, the T cell response, shows significant rat and human T cell immunity.

Figure 8:
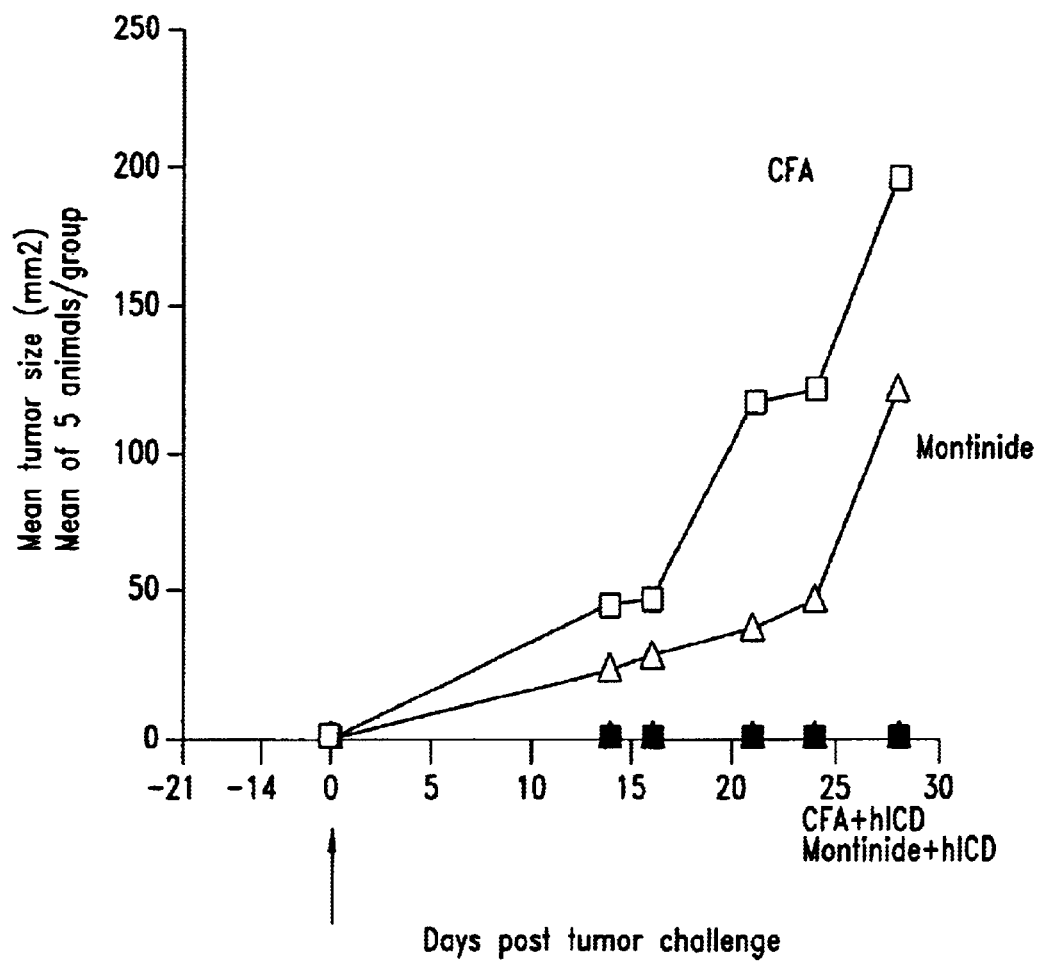
FIG. 8 shows that animals immunized with hICD are protected against tumor challenge.

6. Immunization of animals with hICD protein vaccine protects against tumor challenge. FIG. 8 demonstrates that these immune responses are protective. Animals who received two immunizations with human ICD, a foreign highly homologous protein, prior to tumor implant were totally protected from tumor development as compared to animals who received adjuvant alone.

Example 2

PAP Immunization

A. Materials and Methods

Figure 9B:
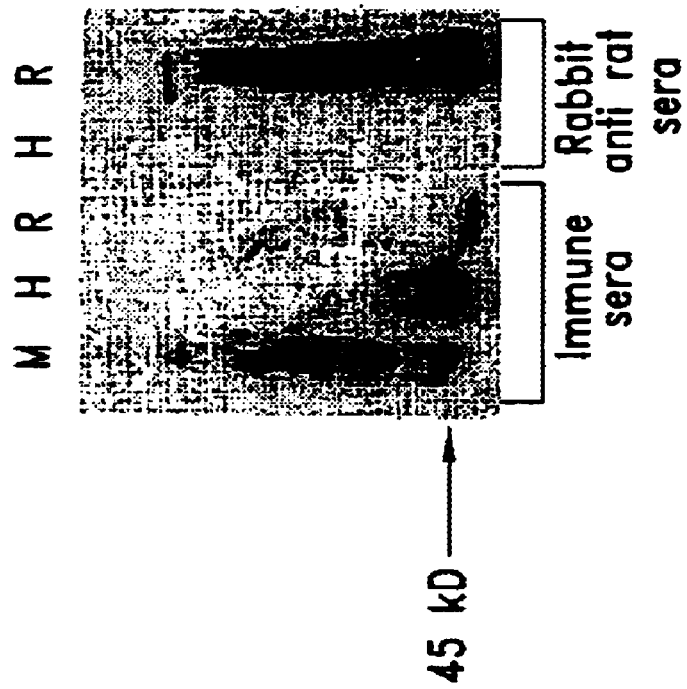
FIGS. 9A–B show Coomassie blue staining and western blot analysis of rat and human prostatic acid phosphatase (PAP). Rat (R) and human (H) PAP were run on a 10%–15% gradient SDS-PAGE gel under reducing conditions, followed by staining with Coomassie blue (A) or western blot analysis (B). The blot was incubated either with sera from female Lewis rat immunized with human PAP (immune sera) or with the polyclonal rabbit anti-rat PAP antibody as a positive control. In the second step, the blots were incubated with HRP-labeled goat anti-rat IgG (Caltag) or HRP-labeled donkey anti-rabbit Ig (Amersham), respectively. The blot was developed with the ECL (Amersham) detection system. The biotinylated molecular weight markers (M) (Biorad) are shown on the left.
Figure 9A:
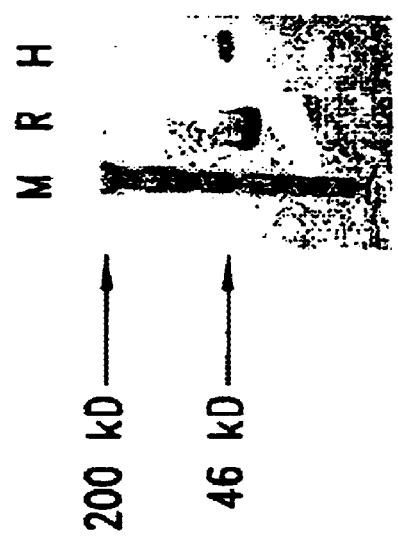

1. Recombinant rat and human PAP were expressed and purified. Recombinant rPAP was obtained from Dr. P. Vihko. rPAP was expressed in baculovirus and purified as described previously. rPAP runs as a 40 kD protein under reducing conditions on a 10–15% SDS gel (FIG. 9A). The protein readily forms dimers when not completely reduced. Recombinant hPAP for use as a homologous foreign protein in the immunization studies was also obtained from Dr. Vihko. Human PAP, expressed in baculovirus, runs as a 45 kD protein under reducing conditions (FIG. 9A) and also has a propensity to form dimers. Polyclonal rabbit anti-rPAP, elicited by immunization with a 15 aa long C-terminal peptide derived from rPAP was specific for recombinant rPAP and did not cross-react with hPAP (FIG. 9B). Polyclonal rat anti-hPAP, elicited by immunization of female Lewis rats with hPAP, cross reacted with human and rPAP (FIG. 9B).

B. Results

Figure 10A:
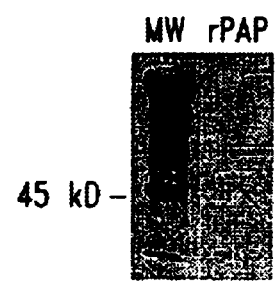
FIGS. 10A–B show that no immunity to rat PAP was induced by immunization with whole rat PAP. Female Lewis rat were immunized with recombinant rat PAP (100 $\mu$g) admixed with CFA and boosted twice with rat PAP plus IFA at three-week intervals. The antibody response against rat PAP (rPAP) was determined by western blot analysis (A) as described in FIG. 1. The T cell response was determined by a standard proliferation assay (B). Histapaque-purified splenic mononuclear cells ($5 \times 10^5$/ml) were incubated with either media, rat PAP (200 $\mu$g/ml), or Con-A (5 $\mu$g/ml) for 96 hours. Tritiated thymidine (1 $\mu$Ci/well) was added to the culture for the last 8 hours. The thymidine uptake by T cells was determined by liquid scintillation counting (cpm).
Figure 10B:
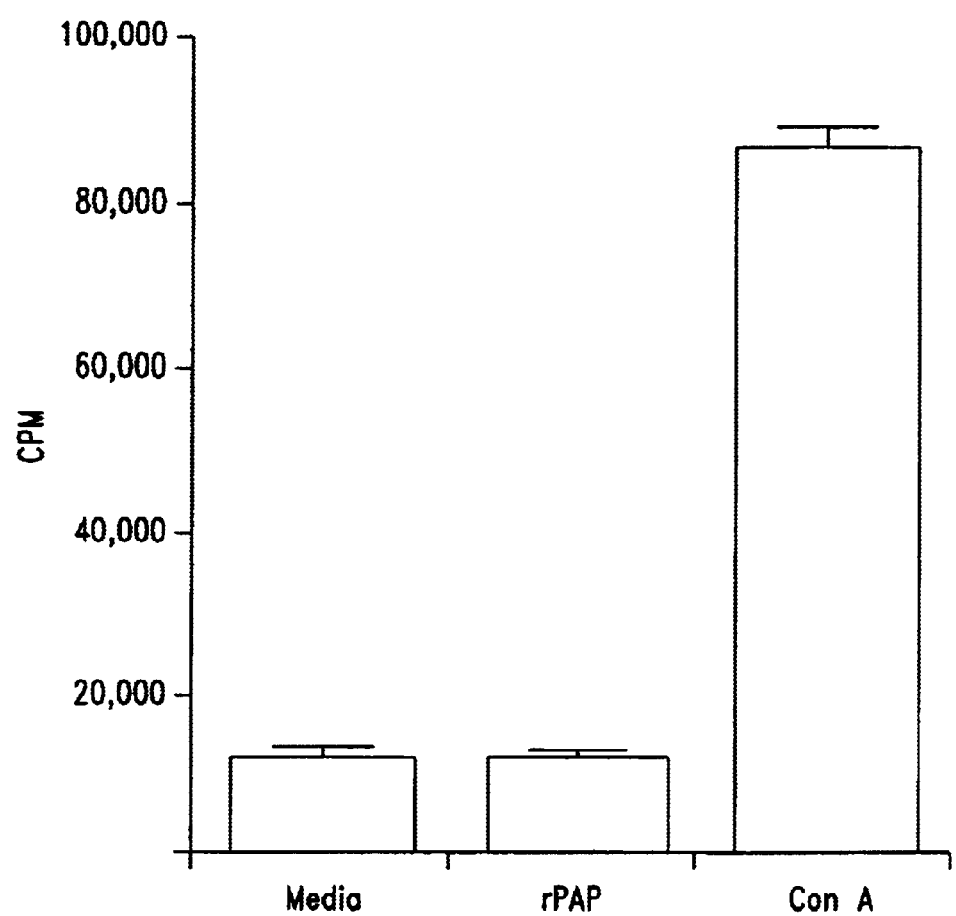
Figure 11:
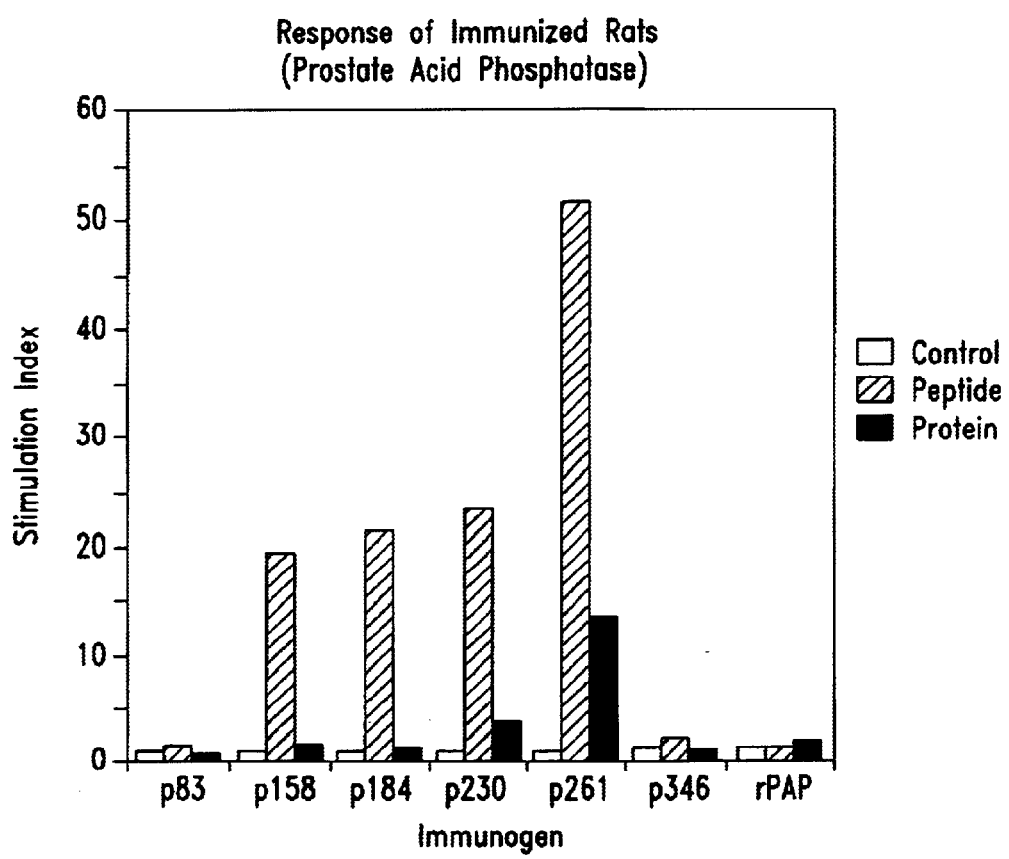
FIG. 11 shows the response to PAP-peptides and whole rat PAP in female rats. 12 week old Fischer (F344) rats were immunized (x3) with individual rat Prostatic Acid Phosphatase (PAP) peptides (100 $\mu$g) as well as whole rat PAP (100 μg), and then tested for a CD4⁺ T cell response to both peptide and protein in a standard proliferation assay. The first immunization was Immunogen+CFA and the subsequent ones were in IFA. The analysis shown was done at the 4th in vitro stimulation.

1. No immunity to rPAP is induced by immunization with native rat PAP protein. Initial experiments tested immunization to PAP in female rats with the presumption that female rats express substantially lower levels of PAP than male rats. This presumption was an extrapolation from human studies in which PAP is not detectable in females. Although female rats are not known to express PAP, some domains of PAP are shared with other phosphatases. Thus, portions of PAP are known to be expressed in females but whether females are tolerant to the whole PAP protein was unknown. Female rats were injected sc. with 100 μg of recombinant rPAP with complete Freund's adjuvant (CFA) and boosted twice with rPAP in incomplete Freund's adjuvant (IFA). No antibody (FIG. 10A) or T cell response to rPAP could be detected (FIG. 10B). In many of the subsequent experiments, serum antibody (IgG) to PAP is used as a surrogate read out for helper T cell immunity.

2. IgG antibody responses to rat PAP can be induced in female rats by concurrent immunization with human PAP and rat PAP. In initial attempts to test for immunization to PAP, immunization with the combination of bovine PAP and rPAP was tested. Female rats were immunized with 100 ug of bovine PAP in CFA x1, followed by 100 ug of rPAP in IFAx2. There was no antibody response to bovine PAP, and no detectable antibody response to rPAP.

Figure 12:
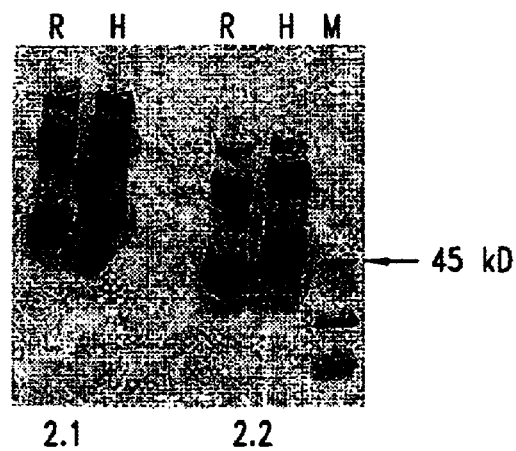
FIG. 12 shows that IgG antibody responses to rat PAP could be induced by sequential immunization with hPAP and rPAP. Female Lewis rats were immunized with human PAP (100 μg) plus CFA. They were boosted at three-week intervals with IFA plus human PAP (100 μg) and with IFA plus rat PAP (100 μg). Antibody responses to rat PAP or human PAP were determined by western blot analysis. Rat PAP (R) and human PAP (H) were run on a 10%–15% SDS-PAGE gel under reducing conditions. The blot was incubated with immune sera from two representative animals (2.1 and 2.2), followed by HRP-labeled goat anti-rat IgG antibody. The blot was developed with the ECL detection system. The molecular weight markers (M) are shown on the right.

Subsequent experiments tested immunization with the combination of hPAP and rPAP. Female Lewis rats were immunized with 100 μg hPAPx2, followed by 100 μg rPAPx1. Strong IgG antibody responses to both hPAP and rPAP were elicited (FIG. 12). As in prior experiments, there was no antibody response to PAP in rats immunized with rPAP alone. Results were reproducible. In two separate experiments, 4/4 and 3/3 rats exhibited a strong antibody responses to both the human and rat proteins.

Figure 13:
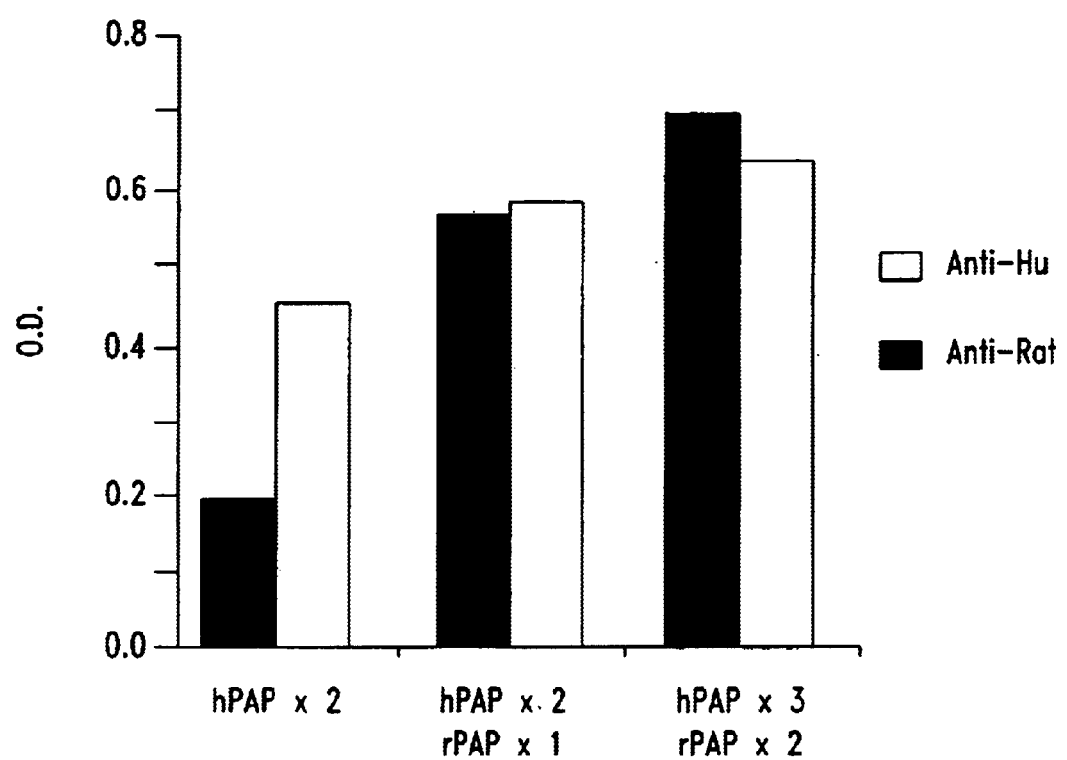
FIG. 13 shows that IgG antibody responses to rat PAP after immunization with human PAP can be significantly boosted by subsequent injections with rat PAP. Female Lewis rats were immunized with human PAP (100 μg) plus CFA. They were boosted sequentially at 3-week intervals with IFA plus human and rat PAP (hPAPx2, rPAPx1); or IFA plus human and rat PAP (hPAPx3, rPAPx2). Sera were obtained two weeks after each boosting. The amount of antibody to rat PAP (solid bars) or human PAP (open bars) in the immune sera was determined by an ELISA assay with 96-well plates pre-coated with either rat PAP or human PAP, respectively. The ELISA assay was developed with HRP-labeled goat anti-rat IgG antibody followed by HRP substrates, and the absorbance at 450 nm was determined.
Figure 14:
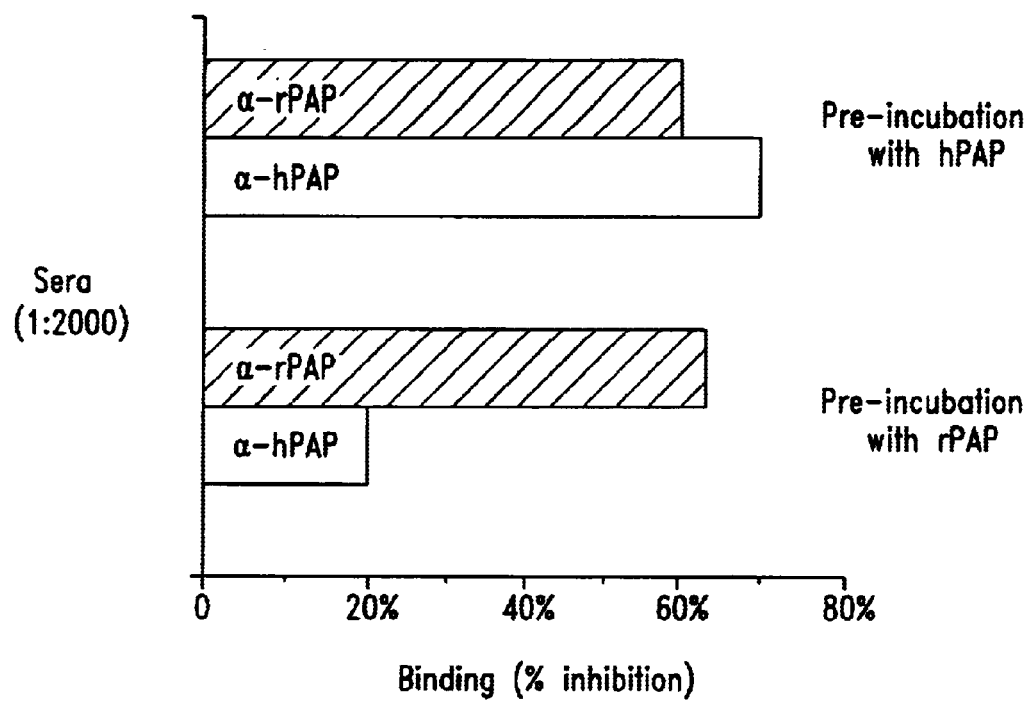
FIG. 14 shows that binding of IgG antibody in immune sera to immobilized rat and human PAP is inhibited significantly by soluble human PAP in an ELISA assay. Sera (1:2000 dilution) from animals immunized with human PAP was pre-incubated with 100 ug/ml of either BSA, human PAP (hPAP) or rat PAP (rPAP) for 2 hours at 4° C. The sera was then added to 96-well plates pre-coated with either rPAP(100 μ/ml) or hPAP(100 μg/ml) to determine the amount of binding to rPAP (solid bars) or hPAP (open bars), respectively, by an ELISA assay. The ELISA assay was developed with HRP-labeled goat anti-rat IgG antibody followed by HRP substrates, and the absorbance at 450 nm was determined. The inhibition of antibody binding to immobilized rPAP and hPAP by pre-incubation of immune sera with either soluble rPAP or hPAP was compared to the binding of immune sera pre-incubated with BSA.

Antibodies to rPAP were reactive primarily to cross-reactive epitopes present on both rPAP and hPAP. Immunization to rPAP alone elicited no antibody (FIG. 10). Immunization to hPAP elicited antibody primarily to hPAP, with a lower response to rPAP (FIG. 13). Immunization to hPAP followed by immunization to rPAP boosted the response to rPAP to a level comparable to the response to hPAP (FIG. 13). Despite the need for immunization with rPAP to elicit the highest level of antibody to rPAP, the epitopes recognized were present on both rPAP and hPAP. This was determined in experiments showing that antibody to rPAP could be absorbed out by incubation with hPAP, but antibody to hPAP could not be absorbed out by incubation with rPAP. In those experiments (FIG. 14) pre-incubation of sera from rats immunized to hPAP plus rPAP (1:2000 dilution), hPAP (100 μg) in the solution phase competed out antibody to both hPAP and rPAP. By contrast, pre-incubation of immune sera with rPAP, successfully competed out only the anti-rPAP response, and did not appreciably effect the anti-hPAP response (FIG. 14).

Figure 15A:
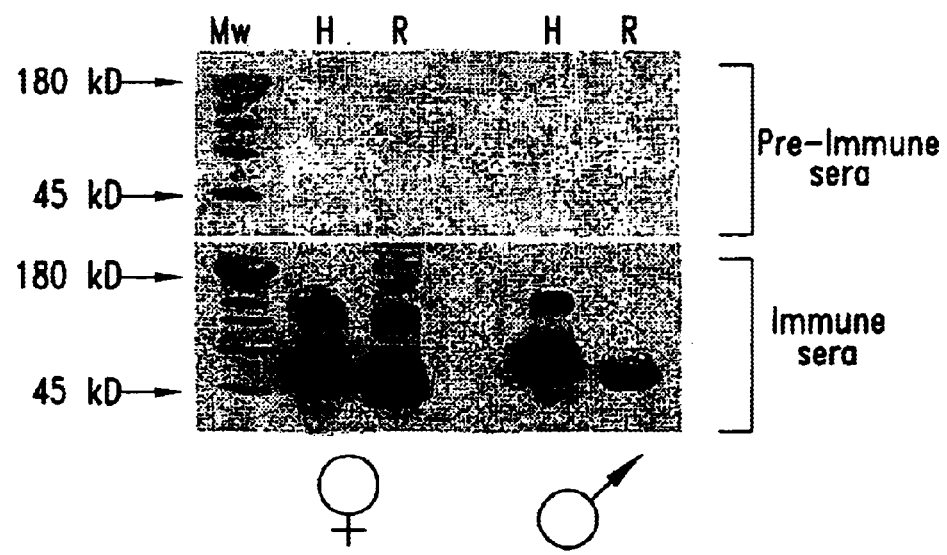
FIG. 15A shows that both female and male rats can be immunized to rPAP by sequential immunization to foreign (human) PAP and rPAP. Female or male Lewis rats were immunized with human PAP and boosted with rat PAP as described in FIG. 5. Sera obtained pre and post immunization was evaluated for a response to rat and human PAP by western blot analysis. Rat PAP (R) and human PAP (H) were run on a 10%–15% SDS-PAGE gel under reducing conditions. The blot was incubated with pre-immune or immune sera, followed by HRP-labeled goat anti-rat IgG antibody.
Figure 15B:
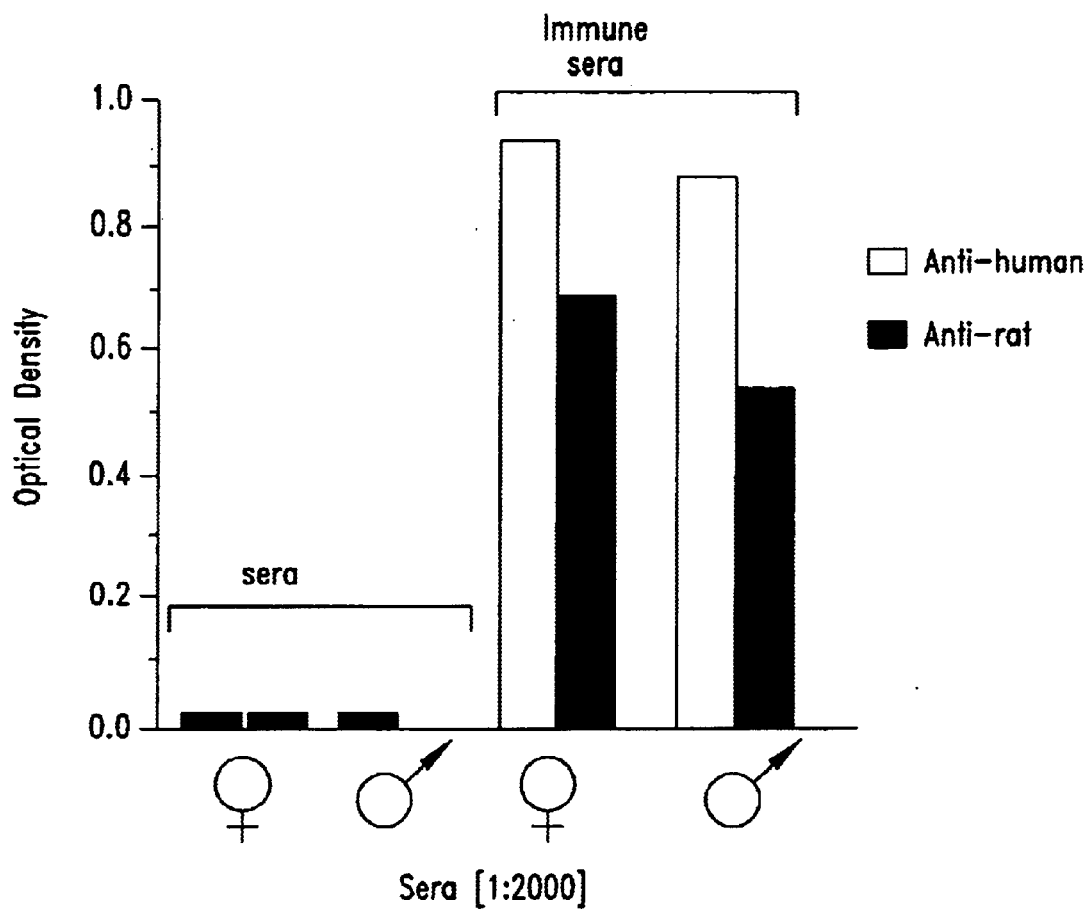
FIG. 15B shows that similar IgG antibody responses to rat and human PAP were detected in male and female rats immunized with human PAP plus rat PAP, as determined by an ELISA assay. Female or male Lewis rats were immunized with human PAP and boosted with rat PAP as described in FIG. 5. Sera obtained pre and post immunization was examined for antibody to rat and human PAP by an ELISA assay. The 96-well plates were first coated either with rat PAP (solid bars) or human PAP (open bars), and then incubated with pre-immune or immune sera (1:2000 dilution). The ELISA assay was developed with HRP-labeled goat anti-rat IgG antibody followed by HRP substrates, and the absorbance at 450 nm was determined.
Figure 16:
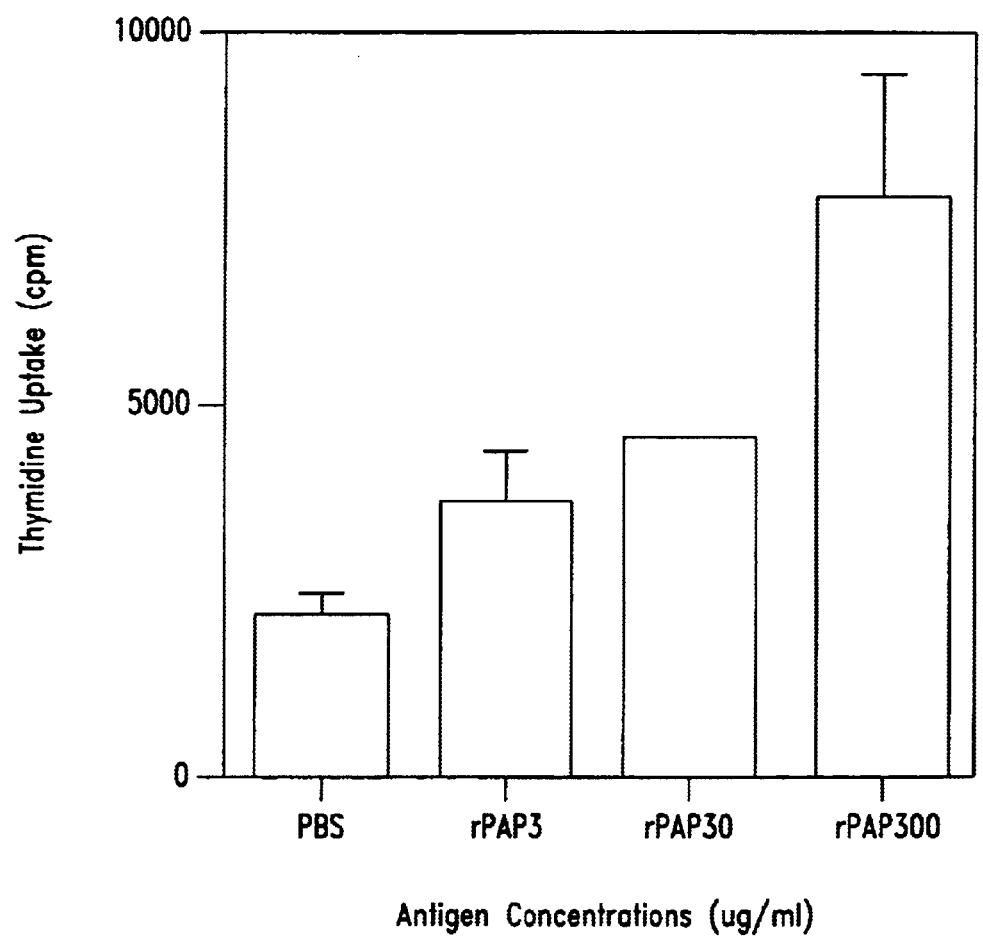
FIG. 16 shows that T cells from rats immunized sequentially to hPAP and rPAP can respond to rat PAP. Splenic T cells from rats immunized sequentially to hPAP and rPAP were stimulated once in vitro with rat PAP and then cultured with PBS or rat PAP (3, 30 and 300 μ/ml) in the presence of irradiated spleen cells as APC for 72 hours. One μCi of ³H-TdR was added to the culture for the last 16 hours. Thymidine uptake was determined by liquid scintillation counting.

3. Antibody and T cell responses to rat PAP can be induced in male rats by sequential immunization with human PAP and rat PAP. In the above experiments, there was a much stronger anti-rPAP antibody response in female rats when animals are immunized sequentially with hPAP plus rPAP, as opposed to concurrent immunization with hPAP plus rPAP. Male rats were immunized with the optimal regimen for immunizing female rats above, i.e., hPAP (100 μg) in CFAx1 and boostedx1 with hPAP and x1 with rPAP in IFA. Male rats developed a robust IgG antibody response to rPAP (FIG. 15A), with the absolute level of response being very comparable to that elicited in female rats in the same experiment (FIG. 15B). Importantly, T cells specific for rPAP were also elicited (FIG. 16).

From the foregoing, it will be evident that, although specific embodiments of the invention have been described herein for purposes of illustration, various modifications may be made without deviating from the spirit and scope of the invention.

What is claimed is:

1. A method of eliciting or enhancing a T cell response to a human self tumor antigen, consisting of immunizing a human being with a composition consisting of:

a protein or a portion thereof with an amino acid sequence native to a non-human source, wherein the non-human protein or portion thereof has at least 80% amino acid sequence homology to the human self tumor antigen but is not identical in amino acid sequence to the human antigen, and wherein the human self tumor antigen is human prostatic acid phosphatase (PAP), and a pharmaceutically acceptable carrier or diluent.

2. A method of eliciting or enhancing a T cell response to a human self tumor antigen, consisting of immunizing a human being with a composition consisting of:

a protein or a portion thereof with an amino acid sequence native to a non-human source, wherein the non-human protein or portion thereof has at least 80% amino acid sequence homology to the human self tumor antigen but is not identical in amino acid sequence to the human antigen, and wherein the human self tumor antigen is human prostatic acid phosphatase (PAP), a pharmaceutically acceptable carrier or diluent, and an adjuvant.

3. A method of eliciting or enhancing a T cell response to a human self tumor antigen, consisting of immunizing a human being with a composition consisting of:

a protein or a portion thereof with an amino acid sequence native to a non-human source, wherein the non-human protein or portion thereof has at least 80% amino acid sequence homology to the human self tumor antigen but is not identical in amino acid sequence to the human antigen, and wherein the human self tumor antigen is human prostatic acid phosphatase (PAP), and an adjuvant.

* * * * *

UNITED STATES PATENT AND TRADEMARK OFFICE
CERTIFICATE OF CORRECTION

PATENT NO. : 6,942,862 B2
DATED : September 13, 2005
INVENTOR(S) : Martin A. Cheever and Mary L. Disis It is certified that error appears in the above-identified patent and that said Letters Patent is hereby corrected as shown below:

Column 1,
Line 13, before the "Technical Field", insert the following:
-- This invention was made with government support under grant numbers R01 CA61912 and R29 CA68255 awarded by the National Instituted of Health. The government may have certain rights in the invention. --.

Signed and Sealed this

Twentieth Day of December, 2005

JON W. DUDAS
*Director of the United States Patent and Trademark Office*